United States Patent [19]
Lowe, III

[11] Patent Number: 5,527,808
[45] Date of Patent: Jun. 18, 1996

[54] FUSED TRICYCLIC NITROGEN CONTAINING HETEROCYCLES

[75] Inventor: John A. Lowe, III, New York, N.Y.

[73] Assignee: Pfizer Inc., New York, N.Y.

[21] Appl. No.: 204,342

[22] PCT Filed: Aug. 20, 1992

[86] PCT No.: PCT/US92/06819

§ 371 Date: Sep. 15, 1994

§ 102(e) Date: Sep. 15, 1994

[87] PCT Pub. No.: WO93/06099

PCT Pub. Date: Apr. 1, 1993

Related U.S. Application Data

[63] Continuation-in-part of Ser. No. 766,488, Sep. 26, 1991, abandoned.

[51] Int. Cl.[6] .................. A61K 31/44; C07D 451/00; C07D 221/02
[52] U.S. Cl. .................. 514/294; 546/94; 546/112
[58] Field of Search .................. 546/94, 112; 514/294

[56] References Cited

U.S. PATENT DOCUMENTS 3,506,673  4/1970  Warawa et al. .................. 546/133
3,534,053  10/1970  Sallay et al. .................. 546/133
5,162,339  11/1992  Lowe, III .................. 546/133

FOREIGN PATENT DOCUMENTS 9005729  5/1990  WIPO.
9201688  2/1992  WIPO.

OTHER PUBLICATIONS

Schneider et al, Arch. Pharm. 309, 447 (1976).

Primary Examiner—Cecilia Tsang
Attorney, Agent, or Firm—Peter C. Richardson; Paul H. Ginsburg; Karen Debenedictis

[57] ABSTRACT

The present invention relates to novel fused tricyclic nitrogen containing heterocyclic compounds, and specifically, to compounds of the formula

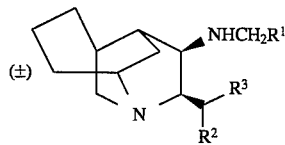

wherein $R^1$, $R^2$ and $R^3$ are as defined below. These novel compounds are useful in the treatment of inflammatory and central nervous system disorders, as well as other disorders.

12 Claims, No Drawings

FUSED TRICYCLIC NITROGEN CONTAINING HETEROCYCLES

This application is a continuation-in-part of U.S application Ser. No. 766,488, which was filed on Sept. 26, 1991, now abandoned.

This application is a 371 application Ser. No. of PCT/US92/06819, filed Aug. 20, 1992.

BACKGROUND OF THE INVENTION

The present invention relates to novel fused tricyclic nitrogen containing herterocycles, pharmaceutical compositions comprising such compounds and the use of such compounds in the treatment and prevention of inflammatory and central nervous system disorders, as well as several other disorders. The pharmaceutically active compounds of this invention are substance P receptor antagonists. This invention also relates to novel intermediates used in the synthesis of such substance P receptor antagonists.

Substance P is a naturally occurring undecapeptide belonging to the tachykinin family of peptides, the latter being named because of their prompt stimulatory action on smooth muscle tissue. More specifically, substance P is a pharmacologically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has been shown to be involved in the transmission of pain or migraine (see B. E. B. Sandberg et al., *Journal of Medicinal Chemistry*, 25, 1009 (1982)), as well as in central nervous system disorders such as anxiety and schizophrenia, in respiratory and inflammatory diseases such as asthma and rheumatoid arthritis, respectively, in rheumatic diseases such as fibrositis, and in gastrointestinal disorders and diseases of the GI tract such as ulcerstive colitis and Crohn's disease, etc. (see D. Regoli in "Trends in Cluster Headache," edited by F. Sicuteri et al., Elsevier Scientific Publishers, Amsterdam, pp. 85–95 (1987)).

In the recent past, some attempts have been made to provide antagonists for substance P and other tachykinin peptides in order to more effectively treat the various disorders and diseases listed above.

Quinuclidine derivatives and related compounds that exhibit activity as substance P receptor antagonists we referred to in Published PCT International Patent Application No. PCT/US89/05338, filed Nov. 20, 1989, now Published PCT International Patent Application No. WO90/06729 (published May 31, 1990) and now also U.S. Pat. No. 5,162,339.

Piperidine derivatives and related heterocyclic nitrogen-containing compounds that are useful as substance P receptor antagonists are referred to in PCT International Patent Application No. PCT/US90/00116, filed Jan. 4, 1990, which is now Published POT International Patent Application No, WO91/09844 (published Jul. 11, 1992).

SUMMARY OF THE INVENTION

The present Invention relates to compounds of the formula

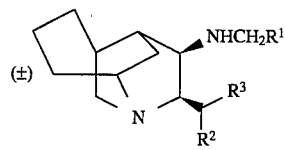

wherein $R^1$ is cycloalkyl having from five to seven carbon atoms, pyrrolyl, thienyl, pyridyl, phenyl or substituted phenyl, wherein said substituted phenyl is substituted with from one to three substituents Independently selected from fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety and benzyloxycarbonyl;

$R^2$ is furyl, thienyl, pyridyl, indolyl, biphenyl, phenyl or substituted phenyl, wherein said substituted phenyl Is substituted with one or two substituents independently selected from fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety and benzyloxycarbonyl; and $R^3$ is thienyl, phenyl, fluorophenyl, chlorophenyl or bromophenyl.

The present Invention also relates to the pharmaceutically acceptable acid addition and base salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The term "halo", as used herein, unless otherwise indicated, includes chloro, fluoro, bromo and iodo.

The term "alkyl", as used herein, unless otherwise indicated, includes saturated monovalent hydrocarbon radicals having straight, branches or cyclic moieties or combinations thereof.

Examples of compounds of the formula I include:

(+)-cis-9-diphenylmethyl-N-((2-methoxyphenyl)methyl)-10-azatricyclo[4.4.1.0$^{5,7}$]undecan-8-amine;

(+)-cis-9-diphenylmethyl-N-(2-methoxy-5-chlorophenyl)-10-azatricyclo[4.4.1.0$^{5.7}$]-undecan-8-amine;

(+)-cis-9-diphenylmethyl-N-(2-trifluoromethoxyphenyl)-10-azatricyclo[4.4.1.0$^{5,7}$]-undecan-8-amine;

(+)-cis-9-diphenylmethyl-N-(2-trifluoromethoxy-5-chlorophenyl)-10-azatricyclo-[4.4.1.0$^{5.7}$]undecan-8-amine;

(+)-cis-9-diphenylmethyl-N-(2-difluoromethoxyphenyl)-10-azatricyclo[4.4.1.0$^{5,7}$]-undecan-8-amine;

(+)-cis-9-diphenylmethyl-N-(2-difluoromethoxy-5-chlorophenyl)-10-azatricyclo-[4.4.1.0$^{5,7}$]undecan-8-amine;

(+)-cis-9-diphenylmethyl-N-(2-methoxy-5-isopropylphenyl)-10-azatricyclo-[4.4.1.0$^{5,7}$]undecan-8-amine;

(+)-cis-9-diphenylmethyl-N-(2-trifluoromethoxy-5-isopropylphenyl)-10-azatricyclo-[4.4.1.0$^{5,7}$]undecan-8-amine;

(+)-cis-9-diphenylmethyl-N-(2-difluoromethoxy-5-isopropylphenyl)-10-azatricyclo-[4.4.1.0$^{5,7}$]undecan-8-amine;

(+)-cis-9-diphenylmethyl-N-(2-methoxy-5fluorophenyl)-10-azatricyclo[4.4.1.0$^{5,7}$]-undecan-8-amine;

(+)-cis-9-diphenylmethyl-N-(2-difluoromethoxy-5-fluorophenyl)-10-azatricyclo [4.4.1.0$^{5,7}$]-undecan-8-amine;

(+)-cis-9-diphenylmethyl-N-(2-methoxy-5-t-butylphenyl)-10-azatricyclo [4.4.1.0$^{5,7}$]-undecan-8-amine;

(+)-cis-9-diphenylmethyl-N-(2-trifluoromethoxy-5-t-butylphenyl)-10-azatricyclo-[4.4.1.0$^{5,7}$]undecan-8-amine; and (+)-cis-9-diphenylmethyl-N-(2-difluoromethoxy-5-t-butylphenyl-10-azatricyclo[4.4.1.0$^{5,7}$]undecan-8-amine.

The invention also relates to compounds of the formula

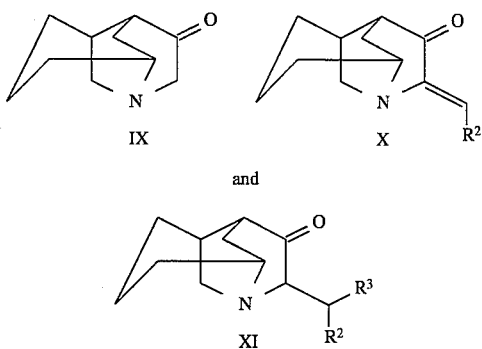

wherein R$^2$ and R$^3$ are defined as above.

This invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in treating or preventing such condition, and a pharmaceutically acceptable carrier.

This invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in treating or preventing such condition.

This invention also relates to a pharmaceutical composition for antagonizing the effects of substance P in a mammal, including a human, comprising a substance P antagonizing amount of a compound of the formula I, or a pharmaceutically acceptable salt thereof, and a pharmaceutically acceptable carrier.

This invention also relates to a method of antagonizing the effects of substance P in a mammal, including a human, comprising administering to said mammal a substance P antagonizing amount of a compound of the formula I, or a pharmaceutically acceptable salt thereof.

This invention also relates to a pharmaceutical composition for treating or preventing a disorder in a mammal, including a human, resulting from an excess of substance P, comprising a substance P antagonizing amount of a compound of the formula I, or a pharmaceutically acceptable salt thereof, and a pharmaceutically acceptable carrier.

This invention also relates to a method of treating or preventing a disorder in a mammal, including a human, resulting from an excess of substance P, comprising administering to said mammal a substance P antagonizing amount of a compound of the formula I, or a pharmaceutically acceptable salt thereof.

This invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in antagonizing the effect of substance P at its receptor site, and a pharmaceutically acceptable carrier.

This invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in antagonizing the effect of substance P at its receptor site.

This invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in antagonizing the effect of substance P at its receptor site, and a pharmaceutically acceptable carrier.

This invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in antagonizing the effect of substance P at its receptor site.

This invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in treating or preventing such disorder, and a pharmaceutically acceptable carrier.

This invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in treating or preventing such disorder.

This compound of the formula I have chiral centers and therefore exist in different enantiomeric forms. This invention relates to all optical isomers and all stereoisomers of compounds of the formula I, and mixtures thereof.

Optically active compounds of the formula I are additionally useful as synthetic intermediates in the preparation of the corresponding racemic mixtures and opposite enantiomers.

Formula I above includes compounds identical to those depicted but for the fact that one or more hydrogen or carbon atoms are replaced by radioactive isotopes thereof (e.g., tritium, nitrogen-15 or carbon-13 isotopes thereof). Such radio-labelled compounds are useful as research and diagnostic tools in metabolism pharmokinetic studies and in binding assays. Specific applications in research include radioligand binding assays, autoradiography studies and in vivo binding studies, while specific applications in the diagnostic area include studies of the substance P receptor in the human brain in in vivo binding in the relevant tissues for inflammation, e.g. immune-type cells or cells that are directly involved in inflammatory bowel disorders and the like.

DETAILED DESCRIPTION OF THE INVENTION

The compounds of the formula I may be prepared as described in the following reaction schemes and discussion. Unless otherwise indicated, $R^1$, $R^2$, and $R^3$ and structural formula I in the reaction schemes and discussion that follow are defined as above.

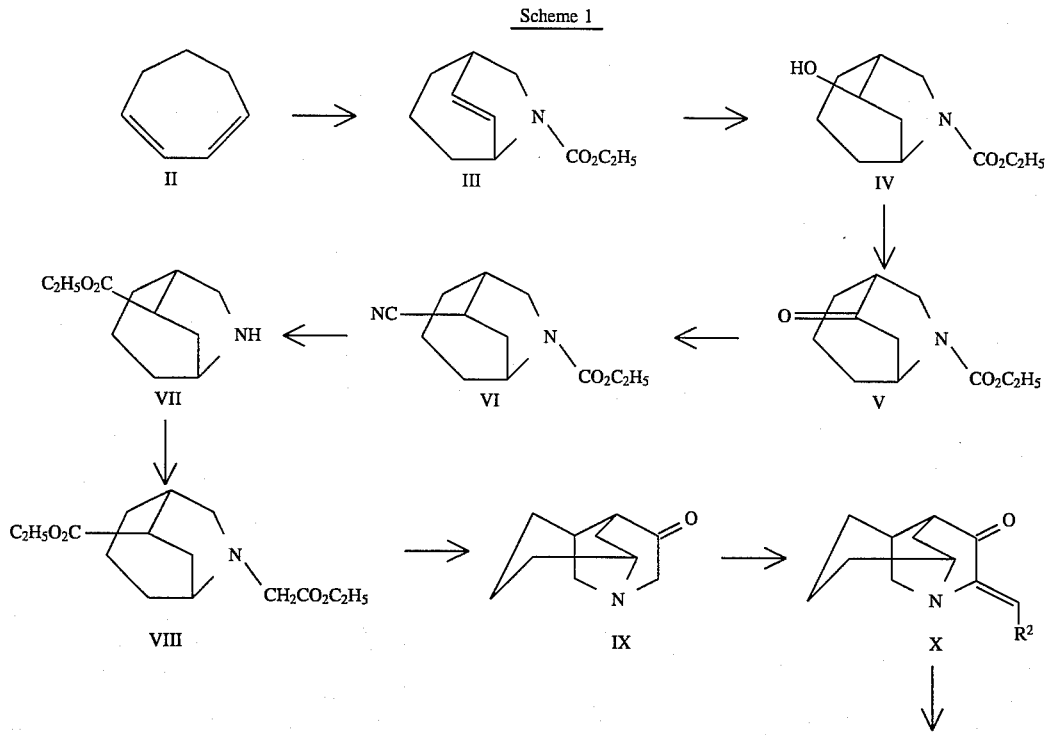

Scheme 1

Scheme 1 (continued)

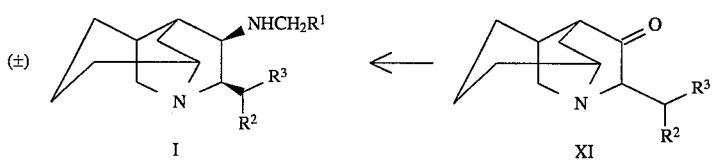

Scheme 2

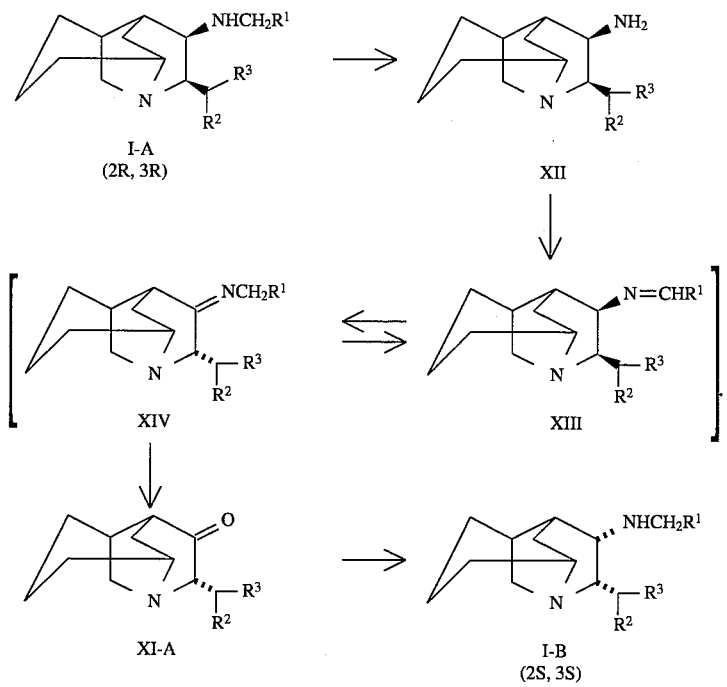

Referring to scheme 1, compounds of the formulae III, IV, V, VI, VII and VIII are homologs of known compounds. The preparation of these compounds from cycloheptadiene is described in Examples 1A–1F.

Compounds of the formulae IX, X, XI and I may be prepared from compound VIII by the following procedure.

Compounds VIII is reacted with an alkali or alkaline earth metal alkoxide, preferably potassium ethoxide. Suitable reaction inert solvents for this reaction include hydrocarbon solvents such as hexane, benzene and toluene. Suitable reaction temperatures range from about room temperature to about the reflux temperature of the solvent. The reflux temperature is preferred. The solvent is evaporated and the residue taken up in a mineral acid such as dilute hydrochloric or dilute surfuric acid. An ethereal hydrocarbon solvent such as dioxane may optionally be used as a cosolvent. Preferably, this reaction is conducted at the reflux temperature of the solvent, but temperatures ranging from about room temperature to about the reflux temperature are also suitable.

The above reaction yields a compound having the formula IX, which is then treated with a compound of the formula $R^2CHO$ to form a compound having formula X. This reaction is typically carded out in a reaction inert aqueous or organic solvent. Suitable solvents include water, lower alcohols, ether, tetrahydrofuran (THF), dimethylformamide (DMF), benzene, toluene, hexane, methylene chloride and chloroform. Ethanol is the preferred solvent. Preferably, the reaction is run in the presence of a basic catalyst. Sodium hydroxide is the preferred catalyst, but other bases such as alkali and alkaline earth metal hydroxides, carbonates and alkoxides, as well as organic amine bases such as trialkylamines and pyridine may also be used. Generally, the reaction is run for about 10 minutes to about 24 hours. The reaction temperature may range from about 0° C. to about 200° C., and is preferably about the reflux temperature of the solvent.

The compound of formula X so formed is then reacted with a compound of the formula $R^3MgX$, wherein X is chloro, fluoro, bromo or iodo, to form a compound of the formula XI. This reaction is usually carried out in a reaction inert hydrocarbon, chlorohydrocarbon or ethereal solvent such as benzene, ether, toluene, hexane, THF or ethyl acetate. The preferred solvent is ether. The reaction is usually run for about 1 minute to about 10 hours. Suitable reaction temperatures range from about −70° C. to about 100° C., with about 0° C. being preferred. The compound of formula XI so formed is then converted to the corresponding desired compound of formula I by reacting it with a compound of the formula $R^1CH_2NH_2$, and then treating the reaction mixture with a reducing agent.

The reaction of the compound of formula XI with $R^1CH_2NH_2$ is typically carried out in a reaction inert hydrocarbon or chlorohydrocarbon solvent, in the presence of an acidic catalyst. Examples of solvents that may be used include hexane, benzene, toluene, chloroform, methylene chloride, ether, THF, and ethyl acetate. Examples of catalysts that may be used include mineral acids, titanium trichloride, molecular sieves and organic acids such as camphor sulfonic acid. Toluene is the preferred solvent and camphor sulfonic acid is the preferred catalyst. This reaction is generally conducted over a period of about 0.5 hours to about 24 hours, at a temperature from about room temperature to about 220° C. Preferably, the reaction temperature is about 110° C.

The reaction mixture is then treated with a reducing agent, as indicated above, to obtain the desired compound of formula I. Reducing agents that may be used include 9-borobicyclononane (9-BBN), triethylsilane and metal hydrides such as sodium borohydride and sodium triacetoxyborohydride. The preferred reducing agent is 9-BBN. Generally, the reduction is carried out in a reaction inert hydrocarbon, chlorohydrocarbon, carboxyhydrocarbon, aqueous or alcoholic solvent. Water, lower alcohols, trifluoroacetic acid, benzene, toluene, ether, hexane, THF, ethyl acetate and chloroform are suitable, with THF being preferred when the reducing agent is 9-BBN. The preferred reaction temperature is about room temperature, but the reduction may be carried out at temperatures ranging from about room temperature to about 200° C.

The 2R,3R enantiomers of the compounds of formula 1 may be converted into the corresponding 2S,3S enantiomers by the following procedure, which is illustrated in Scheme 2.

Referring to scheme 2, the 2R,3R enantiomer having the formula I-A is treated with hydrogen in the presence of a metal containing catalyst such as platinum or palladium. Generally, this reaction is conducted in a reaction inert solvent such as acetic acid or a lower alcohol, at a temperature from about 0° C. to about 50° C. Preferably, the compound of formula I-A is treated with hydrogen in the presence of palladium on carbon in a mixture of methanol/ethanol in water or methanol/ethanol containing hydrochloric acid at a temperature of about 25° C.

The above reaction yields an amine having the formula XII. This amine is then reacted with a compound of the formula $R^1CHO$ in the presence of a drying agent or using an apparatus designed to remove azeotropically the water generated, to produce an imine of the formula XIII. The preparation of the imine is generally carried out in a reaction inert solvent such as benzene, xylene or toluene, preferably toluene, at a temperature from about 25° C. to about 110° C., preferably at about the reflux temperature of the solvent. Suitable drying agents/solvent systems include titanium tetrachloride/dichloromethane, titanium isopropoxide/dichloromethane and molecular sieves/THF. Titanium tetrachloride/dichloromethane is preferred.

The resulting imine of formula XIII is then converted to the corresponding isomeric imine having the formula XIV by reacting it with a strong base such as lithium diisopropylamide or t-butyllithium. An equilibrium between the imines of formulae XIII and XIV results. This reaction is typically conducted in an ethereal solvent such as THF or ethyl ether, at a temperature from about −78° C. to about the reflux temperature of the solvent. It is preferably conducted at the reflux temperature. Hydrolysis of the imine of formula XIV yields the corresponding ketone having the formula XI-A. The hydrolysis is preferably conducted using a mineral acid such as hydrochloric or sulfuric acid, at a temperature from about 0° C. to about 100° C.

The ketone of formula XI-A formula in the preceding step may be converted to the corresponding 2S, 3S enantiomer of formula I-B by the procedure described above and depicted in scheme 1 for converting compounds of the formula XI into compounds of the formula I.

In each of the reactions discussed or illustrated in schemes 1 and 2 above, pressure is not critical unless otherwise indicated. Pressures from about 0.5 atmospheres to about 5 atmospheres are generally acceptable, and ambient pressure, i.e. about 1 atmosphere, is preferred as a matter of convenience.

The novel compounds of the formula I and the pharmaceutically acceptable salts thereof are useful as substance P antagonists, i.e., they possess the ability to antagonize the effects of substance P at its receptor site in mammals, and therefore they are able to function as therapeutic agents in the treatment of the aforementioned disorders and diseases in an afflicted mammal.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the Formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds of the formula I which are also acidic in nature, e.g., where $R^1$ is carboxyphenyl, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of formula I and their pharmaceutically acceptable salts exhibit substance P receptor-binding activity and therefore are of value in the treatment and prevention of a wide variety of clinical conditions the treatment or prevention of which are effected or facilitated by a decrease in substance P mediated neurotransmission. Such conditions include inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways diseaser, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance P antagonists for the control and/or treatment of any of the aforesaid clinical conditions in mammals, including humans.

The compounds of the formula I and the pharmaceutically acceptable salts thereof can be administered via either the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carders include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under stable conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention as substance P antagonists may be determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a $-70°$ C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty- minute period. The pellet is then resuspended in 40 volumes of ice-cold 50 mM Tris buffer (pH 7.7) containing 2 mM of calcium chloride, 2 mM of magnesium chloride, 40 µg/ml of bacitracin, 4µg/ml of leupeptin, 2µg of chymostatin and 200 g/ml of bovine serum albumin. This step completes the production of the tissue preparation.

The radioligand binding procedure is then carried out in the following manner, viz., by initiating the reaction via the addition of 100 µl of the test compound made up to a concentration of 1 µM, followed by the addition of 100 µl of radioactive ligand made up to a final concentration 0.5 mM and then finally by the addition of 800 µl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7,7), with the filters having previously been presoaked for a period of two hours pdor to the filtering procedure. Radioactivity is then determined in a Beta counter at 53% counting efficiency, and the $IC_{50}$ values are calculated by using standard statistical methods.

The anti-psychotic activity of the compounds of the present invention as neuroleptic agents for the control of various psychotic disorders is determined primarily by a study of their ability to suppress substance P-induced or substance P agonist induced hypermotility in guinea pigs. This study is carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The present invention is illustrated by the following examples. It will be understood, however, that the invention is not limited to the specific details of these examples.

EXAMPLE 1

(+)-cis-9-Diphenylmethyl-N-((2-methoxyphenyl) methyl)10-azatricyclo[4.4.1.0$^{5,7}$]-undecan-8-amine dihydrochloride A. N-Carboethoxy-7-azabicyclo[3.2.1]non-8-ene To a 500 mL round-bottomed flask equipped with an addition funnel, a condenser, and a nitrogen inlet were added 20.2 g (0.11 mol) bis(carboethoxyamino)methane (prepared according to *J. Org. Chem.*, 30, 3772 (1965)) and 175 mL benzene. The mixture was cooled to 0° C. and 3.78 g (0.026 mmol) of boron-trifluoride etherate was added, followed by heating to reflux. To the refluxing solution was added 10 g (0.11 mol) cycloheptadiene (prepared according to *J. Chem. Soc.*, 72, 1128 (1950)) dropwise. Refluxing was continued for 1 hour, and the reaction was cooled, washed with aqueous sodium bicarbonate solution, water, and brine, dried over sodium sulfate, and evaporated. The residue was chromatographed on silica gel using hexane/ethyl acetate as eluent to afford an oil, 3.22 g (15%).

$^1$H NMR (CDCl$_3$, δ): 1.04 (triplets, J=7, 3H), 1.1–1.6 (multiplets, 5H), 2.32 (m, 1H), 2.95 (m, 1H), 3.27 (m, 1H), 3.91 (quartets, J=7, 2H), 4.32 and 4.44 (multiplets, 1H), 5.85 (m, 1H), 5.96 (m, 1H).

$^{13}$C NMR (CDCl$_3$, δ): 14.6, 20.8, 28.4, 28.6, 29.2, 29.6, 31.6, 31.8, 49.0, 49.5, 49.7, 49.9, 60.7, 60.8, 128.8, 129.2, 1 31.6, 132.3, 155.3, 155.6.

IR (neat, cm.$^{-1}$): 1692 (C=O).

MS (%): 195 (parent, 88), 166 (98), 108 (61), 94 (84), 93 (64), 81 (64), 80 (100), 79 (72).

Anal. Calc'd. for $C_{11}H_{17}NO_2 \cdot 0.25H_2O$: C 66.14, H 8.83, N 7.01. Found: C 66.53, H-8:64, N 7.05.

B. N-Carboethoxy-7-azabicyclo[3.2.1]nonan-9-ol

To a 500 mL round-bottomed flask equipped with a nitrogen inlet were added 20.0 g (0,103 mol) N-carboethoxy-7-azabicyclo[3.2.1]non-8-ene and 200 mL tetrahydrofuran. To the solution were added 52.7 g (0.124 mol) mercuric trifluoroacetate, and the reaction was stirred at room temperature for 5 days with the addition of 10 g additional mercuric trifluoroacetate. Then, 50 mL 3N aqueous sodium hydroxide were added, followed by a solution of 17.6 g (0.463 mol) sodium borohydride in 210 mL 3N aqueous sodium hydroxide with cooling. After the reaction had subsided, the layers were separated and the aqueous layer was washed with ethyl acetate. The organic layers were added over magnesium sulfate, filtered through Celite®, evaporated and used directly in the next step.

MS (%): 213 (parent, 73), 184 (100), 152 (73), 140 (77).

C. N-Carboethoxy-7-azabicyclo[3.2.1]nonan-9-one

To a 125 mL round-bottomed flask equipped with a nitrogen inlet were added 3.52 g (16.51 mmol) N-carboethoxy-7-azabicyclo[3.2.1]nonan-9-ol and 36 mL acetone. The solution was cooled to 0° C. and 6 mL of a 2.75 M solution of chromium trioxide in sulfuric acid/acetone (Jones' reagent) was added. The reaction was allowed to warm to room temperature and stirred for 2 hours. It was then poured into water and diluted with ether. After washing the aqueous layer with ether, the combined organic layers were filtered through Florosil® and evaporated. The residue was chromatographed on silica gel using hexane/ethyl acetate as eluent to afford an oil, 1.57 g (45%).

$^1$H NMR (CDCl$_3$, δ): 1.14 (triplets, 3H), 1.35 (m, 1H), 1.5–1.9 (m, 4H), 1.98 (m, 1H), 2.28 (m, 1H), 2.48 (m, 1H), 2.5–2.6 (m, 1H), 3.40 (m, 1H), 3.66 (m, 1H), 4.03 (quartets, 2H), 4.41 and 4.53 (multiplets, 1H).

$^{13}$C NMR (CDCl$_3$, δ): 14.6, 19.9, 19.94, 20.1,29.8, 30.1, 32.9, 33.3, 42.7, 42.9, 46.0, 46.7, 46.78, 46.83, 47.9, 48.0, 61.28, 61.33, 61.4, 155.6, 210.8.

IR (neat, cm.$^1$): 1725 and 1690 (C=O).

MS (%): 211 (parent, 53), 212 (51), 169 (57), 166 (100), 140 (72), 96 (72).

HRMS: Calc'd. for $C_{11}H_{17}NO_3$: 211.1209. Found: 211.1208.

D. 9-Cyano-N-carboethoxy-7-azabicyclo[3.2.1]nonane

To a 125 mL round-bottomed flask equipped with a condenser and nitrogen inlet were added 1.5 g (7.11 mmol) N-carboethoxy-7-azabicyclo[3.2.1]nonan-9-one, 36 mL 1,2-dimethoxyethane, and 3.19 g (16.35 mmol) tosylmethylisocyanide. The reaction was cooled to 0° C. and 0.95 mL (16.35 mmol) ethanol was added, followed by portionwise addition of 2.79 g (24.88 mmol) potassium t-butoxide. The reaction was warmed and stirred at 60° C. overnight. It was then concentrated, partitioned between ethyl acetate and water, and the organic layer washed with brine, dried over sodium sulfate and evaporated. The residue was chromatographed on silica gel using hexane/ethyl acetate as eluent to afford 1.00 g (63%) of an oil.

$^1$H NMR (CDCl$_3$, δ): 1.17 and 1.19 (triplets, 3H), 1.38 (m, 1H), 1.5–1.8 (m, 4H), 1.88 (m, 1H), 2.11 (m, 2H), 2.37 (m, 1H), 2.8–2.9 (m, 1H), 3.21 and 3.39 (multiplets, 1H), 3.57 (m, 1H), 4.08 (quartets, 2H), 4.2-4.4 (multiplets, 1H).

$^{13}$C NMR (CDCl$_3$, δ): 14.7, 19.67, 19.72, 20.0, 20.1,24.5, 24.6, 23.3, 23.4, 29.8, 30.0, 30.1,30.3, 30.5, 32.2, 32.30, 32.34, 32.5, 33.4, 33.5, 34.0, 34.2, 34.3, 34.4, 44.7, 44.9, 46.4, 46.6, 46.9, 47.1, 47.9, 48.0, 60.3, 61.2, 121.9, 122.8, 122.9, 155.7.

IR (neat, cm.$^{-1}$): 2210 (CN), 1690 (C=O).

MS (%): 222 (parent, 100), 223 (92), 149 (86), 107 (84), 82 (62).

HRMS: Calc'd. for $C_{12}H_{18}N_2O_2$: 222.1404. Found: 222.1371.

E. Ethyl-7-azabicyclo[3.2.1]nonane-9-carboxylate

To a 125 mL round-bottomed flask equipped with a condenser and nitrogen inlet were added 1.0 g (4.50 mmol) 9-cyano-N-carboethoxy-7-azabicyclo[3.2.1]nonane and 30 mL 6N hydrochloric acid. The reaction was refluxed for 24 hours, cooled, and concentrated. The residue was taken up in 30 mL ethanol and refluxed for 24 hours. The residue was used directly in the following step.

MS (%): 197 (parent, 16), 183 (41), 124 (100), 96 (54), 82 (49), 80 (52).

F. Ethyl-N-carboethoxymethyl-7-azabicyclo[3.2.1]nonane-9-carboxylate

To a 125 mL round-bottomed flask equipped with condenser and nitrogen inlet were added the residue from part E above, 0.94 mL (6.74 mmol) triethylamine, 0.75 mL (6.74 retool) ethyl bromoacetate, and 22 mL ethanol. The reaction was refluxed for 4 days, cooled, and concentrated. The residue was taken up in methylene chloride, washed with aqueous sodium bicarbonate solution, dried over sodium sulfate, filtered, and evaporated. The residue was chromatographed on silica gel using hexane/ethyl acetate-as eluent to afford 391 mg (30%) of an oil.

$^1$H NMR (CDCl$_3$, δ): 1.45 (triplets, 6H), 1.3–1.8 (m, 6H), 2.2–2.4 (m, 2H), 2.58 cm, 1H), 2.73 (m, 2H), 2.79 (m, 1H), 3.29 and 3.30 (singlets, 2H), 4.03 (quartets).

$^{13}$C NMR (CDCl$_3$, δ): 14.2, 20.8, 26.2, 33.1, 33.6, 33.9, 38.9, 52.2, 54.3, 58.3, 60.26, 60.34, 171.6, 175.87, 175.92.

IR (neat, cm.$^{-1}$): 1730 (C=O).

MS (%): 283 (parent, 15), 211 (39), 210 (100), 182 (20), 79 (23), 67 (25), 55 (28).

G. 10-Azatricyclo[4.4.1.0$^{5,7}$]undecan-8-one

To a 100 mL three-neck round-bottom flask equipped with a condenser and nitrogen inlet were added 0.43 g-atm (11.02 mmol) potassium and 22 mL toluene. The reaction was brought to reflux, and 0.65 mL (11.02 mmol) ethanol was added slowly. Once the potassium has been converted to the ethoxide, a solution of 1.25 g (4.41 mmol) ethyl-N-carboethoxymethyl-7-azabicyclo[3.2.1]nonane-9-carboxylate in 5 mL toluene was added, and refluxing continued overnight. The reaction was then cooled and concentrated, taken up in 25 mL 1N hydrochloric acid, and refluxed for 8 hours. After cooling, the mixture was washed with methylene chloride, the pH adjusted to 14 with 6N sodium hydroxide, and the aqueous layer was extracted with methylene chloride. The organic layer was dried over sodium sulfate and evaporated, and the residue used directly in the next step.

H. 9-Phenylmethylene-10-azatdcyclo[4.4.1.0$^{5,7}$]undecan-8-one

To a 25 mL round-bottomed flask equipped with a condenser and nitrogen inlet were added the residue from part G above (68 mg), 66 mg (0.62 mmol) benzaldehyde, 2 mL ethanol, and 10 mg powdered sodium hydroxide. The reaction was refluxed for 25 minutes, cooled, and evaporated. The residue was taken up in methylene chloride, washed with water, dried over sodium sulfate, and evaporated. The residue was chromatographed on a silica gel thick layer plate, developing with hexane/ethyl acetate to afford 76 mg (73%), of an oil.

$^1$H NMR (CDCl$_3$, δ): 1.4–2.4 (n, 8H), 2.52, 2.63, and 2.80 (multiplets, 2H), 3.25, 3.44, and 3.59 (multiplets, 3H), 6.68 and 6.84 (singlets, 1H), 7.2–7.4, 7.81, and 8.00 (multiplets, 5H). $^{13}$C NMR (CDCl$_3$, δ): 19.4, 22.3, 25.5, 26.3, 27.1, 27.2, 29.3, 29.4, 31.9, 37.3, 45.3, 47:0, 51.4, 52.3, 59.1, 59,7, 116,6, 123.1,128.4, 129.2, 129.3, 130.81,130.87, 130.91, 131.7, 133.9, 134.1,145.8, 149.9, 207.2, 207.5.

IR (neat, cm.$^{-1}$): 1730 and 1710 (C=O). MS (%): 253 (parent, 100), 170 (45), 117 (96), 116 (43), 109 (80), 67 (79).

I. 9-Diphenylmethyl-10-azatricyclo[4.4.1.0$^{5,7}$]undecan-8-one

To a 100 mL three-neck round-bottomed flask equipped with a condenser and nitrogen inlet was added 0.71 mL (4.21 mmol) of a 3M solution of phenyl magnesium bromide in ether. The solution was cooled to 0° C. and a solution of 818 mg (3.24 mmol) 9-phenylmethylene-10-azatricyclo[4.4.1.0$^{5,7}$]undecan-8-one in 16 mL toluene was added. The reaction was warmed to room temperature, stirred for 2 hours, and then quenched with aqueous ammonium chloride solution. The reaction was extracted with ethyl acetate, and the organic layer was dried over sodium sulfate and evaporated. The residue was chromatographed on silica gel using hexane/ethyl acetate as eluent to afford an oil, 196 mg (18%). This material gave a solid from isopropanol, mp 178–181° C.

$^1$H NMR (CDCl$_3$, δ): 1.5–2.7 (multipicts, 10H), 3.62 (m, 1H), 4.20 (d, J=6, 1H), 4.67 (d, J=6, 1H), 6.4–6.6 and 7.1–7.6 (m, 10H).

$^{13}$C NMR (CDCl$_3$, δ): 19.5, 22.8, 24.2, 28.7, 28.8, 29.0, 29.5, 29.8, 36.8, 43.6, 46.5, 46.6, 47.5, 48.1, 54.7, 65.2, 70.8, 126.2, 126.3, 126.6, 126.7, 126.99, 127.05, 127.03, 127.05, 127.3, 127.5, 127.6, 127.7, 127.8, 127.89, 127.95, 128.0, 128.2, 128.4, 127.5, 128.7, 129.2, 129.4, 141.0, 142.3, 144.6.

IR (neat, cm.$^{-1}$): 1730 (C=O).

MS (%): 332 (parent+1, <1), 303 (45, parent-CO), 180 (40), 136 (100).

J. (+)-cis-9-Diphenylmethyl-N-((2-methoxyphenyl)methyl)-10-azatricyclo-4.4.1.0$^{5,7}$]undecan-8-amine dihydrochloride To a 25 mL round-bottomed flask equipped with a condenser and nitrogen inlet were added 179 mg (0.54 mmol) 9-diphenylmethyl-10-azatricyclo[4.4.1.0$^{5,7}$]undecan-8-one, 111 mg (0.81 mmol) 2-methoxybenzylamine, 2 mg camphorsulfonic acid, and 3 mL toluene. The reaction was refluxed 2 days, cooled, and 2.2 mL (1.08 mmol) of a 0.5 M solution of 9-borabicyclo[3.3.1]nonane in tetrahydrofuran were added. The reaction was stirred at room temperature for 7 days, and then poured into aqueous 1N hydrochloric acid and extracted with methylene chloride. The aqueous layer was adjusted to pH 14 with 6N sodium hydroxide and extracted with methylene chloride. The organic layer was dried over sodium sulfate and evaporated, and the residue chromatographed on silica gel using methanol/methylene chloride as eluent to afford an oil, 47 mg (19%). The oil was converted to its hydrochloride salt in ether to afford a solid, mp 200–210° C.

$^1$H NMR (CDCl$_3$, δ): 1.40 (dd, J=8,12, 1H), 1.6-2.1 (m, 7H), 2.16 (m, 1H), 2.72 (m, 1H), 2.85 (dd, J=5,7, 1H), 3.02 (m, 1H), 3.13 (m, 1H), 3.38 (m, 1H), 3.45 (dd, J=14,98, 2H), 3.58 and 3.59 (singlets, 3H), 3.71 (dd, J=7.6, 11.7, 1H), 4.43 (d, J=11.7) and 4.57 (d, J=12) (2H), 6.6–6.8 and 7.0–7.4 (m, 14H).

$^{13}$C NMR (CDCl$_3$, δ): 19.7, 20.0, 26.4, 26.7, 28.7, 29.0, 29.3, 29.5, 31.9, 32.2, 33.3, 44.4, 46.3, 46.5, 49.2, 52.3, 52.7, 55.0, 55.1, 55.2, 55.9, 56.6, 61.5, 63.4, 110.0, 120.2, 125.6, 126.3, 127.6, 127.7, 127.8, 128.0, 128.1,128.29, 128.33, 128.9, 129.0, 129.2, 143.3, 145.6, 157.4.

IR (neat, cm.$^{-1}$): 1605 (C=C).

MS (%): 452 (1, parent), 285 (100), 276 (91), 121 (73), 91 (71).

Anal. Calc'd. for C$_{31}$H$_{36}$N$_2$O·2HCl·3H$_2$O: C 64.24, H 7.65, N 4.83. Found: C 63.86, H 7.28, N 4.75.

I claim:
1. A compound of the formula

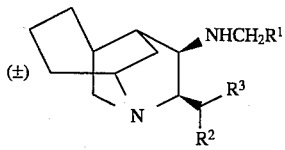

wherein R$^1$ is cycloalkyl having from five to seven carbon atoms, pyrrolyl, thienyl, pyridyl, phenyl or substituted phenyl, wherein said substituted phenyl is substituted with from one to three substituents independently selected from fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety and benzyloxycarbonyl;

R$^2$ is furyl, thienyl, pyddyl, indolyl, biphenyl, phenyl or substituted phenyl, wherein said substituted phenyl is substituted with one or two substituents independently selected from fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety and benzyloxycarbonyl; and R$^3$ is thienyl, phenyl, fluorophenyl, chlorophenyl or bromophenyl; or a pharmaceutically acceptable salt thereof.

2. A compound according to claim 1, wherein R$^1$ is phenyl or substituted phenyl.

3. A compound according to claim 2 wherein R$^1$ is methoxyphenyl.

4. A compound according to claim 3 wherein R$^1$ is 2-methoxyphenyl.

5. A compound according to claim 1 wherein R$^2$ and R$^3$ are independently selected from phenyl, 4-fluorophenyl or thienyl.

6. A compound according to claim 5 wherein each of R$^2$ and R$^3$ is phenyl.

7. A compound according to claim 1, wherein said compound is (+)-cis-9-diphenylmethyl-N-((2-methoxyphenyl) methyl)-10-azatricyclo [4.4.1.0$^{5,7}$]undecan-8-amine.

8. A compound of the formula

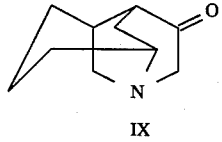 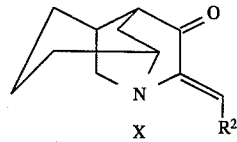

or

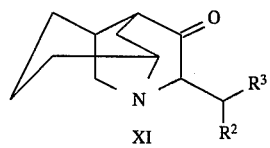

wherein R$^2$ is furyl, thienyl, pyridyl, indolyl, biphenyl, phenyl or substituted phenyl, wherein said substituted phenyl is substituted with one or two substituents independently selected from fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety and benzyloxycarbonyl; and R$^3$ is thienyl, phenyl, fluorophenyl, chlorophenyl or bromophenyl.

9. A pharmaceutical composition for treating a condition selected from the group consisting of inflammatory diseases, anxiety, colitis, depression or dysthymic disorders, psychosis, pain, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, diabetic, disorders related to immune enhancement or suppression and rheumatic diseases in a mammal, comprising an amount of a compound according to claim 1 effective in preventing or treating such condition and a pharmaceutically acceptable carrier.

10. A method of treating a condition selected from the group consisting of inflammatory diseases anxiety, colitis, depression or dysthymic disorders, psychosis, pain, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, diabetic neuropathy disorders, disorders related to immune enhancement or suppression and rheumatic diseases in a mammal, comprising administering to a mammal in need of such treatment an amount of a compound according to claim 1 effective in treating such condition.

11. A pharmaceutical composition for treating a condition in a mammal, the treatment which is effected or facilitated by a decrease in substance P mediated neurotransmission, comprising an amount of a compound according to claim 1 effective in antagonizing the effect of substance P at its receptor site and a pharmaceutically acceptable carrier.

12. A method of treating a condition in a mammal, the treatment of which is effected or facilitated by a decrease in substance P mediated neurotransmission, comprising administering to a mammal in need of such treatment an amount of a compound according to claim 1, or a pharmaceutically acceptable salt thereof, effective in antagonizing the effect of substance P at its receptor site.

* * * * *